(12) United States Patent
Wozniak

(10) Patent No.: US 7,900,281 B2
(45) Date of Patent: Mar. 8, 2011

(54) PROTECTIVE DEVICE, SUCH AS SAFETY WORK GOGGLES, BOW-TYPE EAR PROTECTOR, OR THE LIKE

(75) Inventor: Cordula Wozniak, Nürnberg (DE)

(73) Assignee: Uvex Arbeitsschutz GmbH, Fürth (DE)

( * ) Notice: Subject to any disclaimer, the term of this patent is extended or adjusted under 35 U.S.C. 154(b) by 705 days.

(21) Appl. No.: 11/926,985

(22) Filed: Oct. 29, 2007

(65) Prior Publication Data

US 2008/0120766 A1 May 29, 2008

(30) Foreign Application Priority Data

Nov. 29, 2006 (DE) .................. 10 2006 056 219

(51) Int. Cl.
*A61F 9/02* (2006.01)
(52) U.S. Cl. .................. 2/448; 2/209; 16/228
(58) Field of Classification Search .............. 2/209, 448; 16/225–228; 181/129
See application file for complete search history.

(56) References Cited

U.S. PATENT DOCUMENTS

| | | | |
|---|---|---|---|
| 2,108,074 A * | 2/1938 | McMahon | 2/445 |
| 3,944,344 A * | 3/1976 | Wichers | 351/41 |
| 4,323,244 A | 4/1982 | Busing | |
| 4,671,265 A * | 6/1987 | Andersson | 128/866 |
| 4,679,817 A | 7/1987 | Schufer | |
| 5,022,389 A | 6/1991 | Brennan | |
| 5,059,017 A * | 10/1991 | Bennato | 351/121 |
| 6,123,168 A * | 9/2000 | Berg et al. | 181/129 |
| 6,421,837 B1 * | 7/2002 | Pearcy | 2/171 |
| 6,779,887 B2 * | 8/2004 | Meiler | 351/153 |
| 2004/0032564 A1 | 2/2004 | Meiler | |

FOREIGN PATENT DOCUMENTS

| | | |
|---|---|---|
| DE | 1229751 B | 12/1966 |
| DE | 29611562 U1 | 1/1986 |
| DE | 29611562 U1 | 5/1996 |
| DE | 10226103 C1 | 10/2003 |
| DE | 102004023884 A1 | 8/2005 |
| GB | 1056999 | 2/1967 |
| GB | 1108209 A | 4/1968 |
| GB | 2161060 A | 1/1986 |

OTHER PUBLICATIONS

German Search Report issued in connection with the priority application DE 10 2006 056 219.4.

* cited by examiner

*Primary Examiner* — Katherine Moran
(74) *Attorney, Agent, or Firm* — Browdy and Neimark PLLC

(57) ABSTRACT

In a protective device for the human body, in particular a bow-type ear protector, a pair of safety work goggles, or the like, that includes a joint between two parts that are to be joined in articulated fashion that is formed by a film hinge in the form of a strap hinge injection-molded integrally with the parts to be joined, it is provided that in addition to the first strap hinge, a second strap hinge, also injection-molded integrally with the parts to be joined, is provided, which can be folded up and which is disposed in the joint region at a spacing from the first strap hinge.

8 Claims, 2 Drawing Sheets

PROTECTIVE DEVICE, SUCH AS SAFETY WORK GOGGLES, BOW-TYPE EAR PROTECTOR, OR THE LIKE

BACKGROUND OF THE INVENTION

1. Field of the Invention

The invention is directed to a protective device for the human body, in particular a bow-type ear protector, safety work goggles, or the like, including a joint between two parts to be joined in articulated fashion, which joint is formed by a film hinge in the form of a strap hinge injection-molded integrally with the parts to be joined.

2. Background Art

One such protective device, in the form of a bow-type ear protector, is known for instance from German utility model DE 296 11 562 U1.

Such known embodiments have the disadvantage that the film hinge has relatively low torsional strength, which makes the entire arrangement unstable and sometimes leads to insufficient durability.

SUMMARY OF THE INVENTION

With this as the point of departure, it is the object of the invention to create a protective device or a film hinge, in which high torsional stability is attained in the joint region along with ease of manufacture.

This object is attained according to the invention in that in addition to the first strap hinge, a second strap hinge, also injection-molded integrally with the parts to be joined, is provided, which can be folded up and which is disposed in the joint region at a spacing from the first strap hinge.

This second strap hinge, together with the first strap hinge, forms a kind of box profile with high rotational stability. While the first strap hinge, in the conventional way, joins the parts to be joined such that they are immediately adjacent one another, according to the invention the second strap hinge is provided with a fold, which upon closure of the joint, or in other words in the extended position of the parts to be joined, either protrudes outward when folded up or when folded up extends into the interior of the hinge region.

In other words, when folded, the second strap hinge extends across the joint opening range that is defined by the first strap hinge.

In the hinge region of the first strap hinge, the second strap hinge can extend away from the outer edges of the parts to be joined; however, that has the disadvantage that in the extended state, the second strap hinge protrudes outward.

It is therefore preferably provided that the parts to be joined each have an oblique face, opening outward, on their respective end faces in the joint region, and the second strap hinge extends inward away from the transitional edges between the face end and the respective oblique face and comes to rest, in the open state of the joint, in folded-up fashion in the interior of the joint.

To enable manufacturing the joint in a simple and economical way by means of a so-called open-and-closed injection mold, it is provided that the joint has no portions that protrude in the direction of the hinge axes.

For attaining a final positional stability in the extended state, it may be provided that on the face ends of the parts to be joined in articulated fashion, at least one protrusion, for instance in the form of a detent rib, is provided, and on the respective other part, at least one detent recess, for instance in the form of a detent groove is provided.

The invention is also directed to a film hinge, in particular for a body protection product, such as a bow-type ear protector or a pair of safety work goggles, including at least one joint strap, injection-molded integrally with two parts to be joined in articulated fashion, which is distinguished in that in addition to the first strap hinge, a second strap hinge, also injection-molded integrally with the parts to be joined, is provided, which can be folded up and which is disposed in the joint region at a spacing from the first strap hinge.

The invention is described in further detail below in terms of a preferred exemplary embodiment in conjunction with the drawings.

DESCRIPTION OF THE PREFERRED EMBODIMENT

Figure 1:
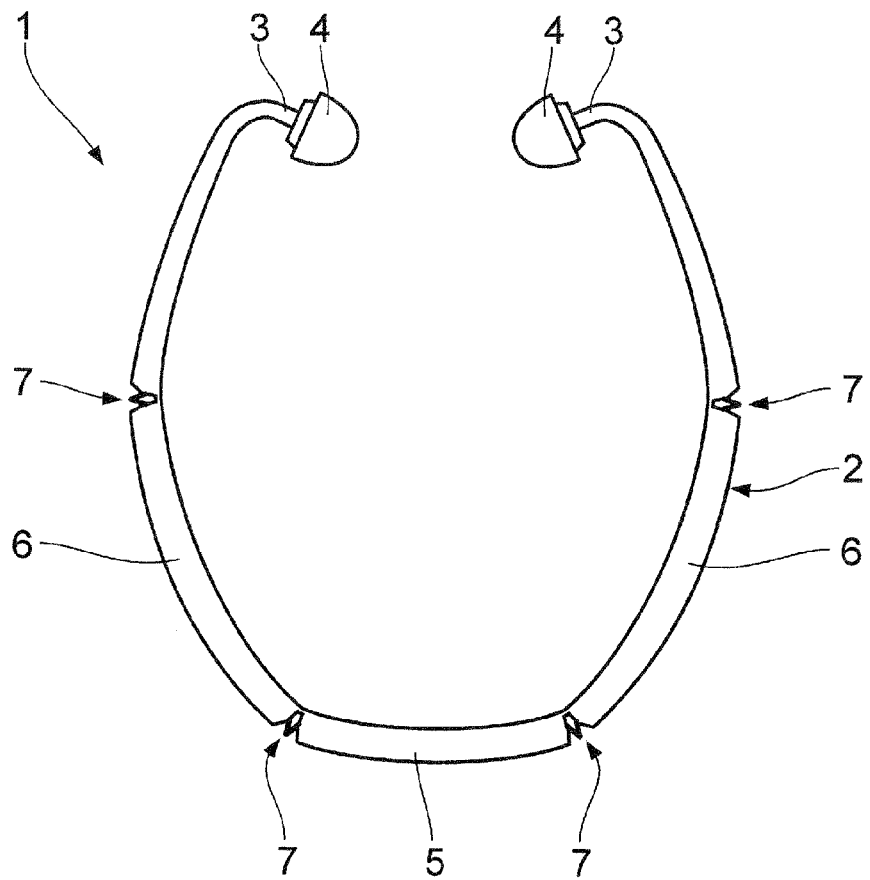
FIG. 1 shows a bow-type ear protector, with film hinges according to the invention, in the open state for use.

In FIG. 1, a bow-type ear protector 1 is schematically shown, including a substantially U-shaped bow 2, on the free ends 3, bent at a right angle, of which protective earplugs 4 are disposed.

Figure 2:
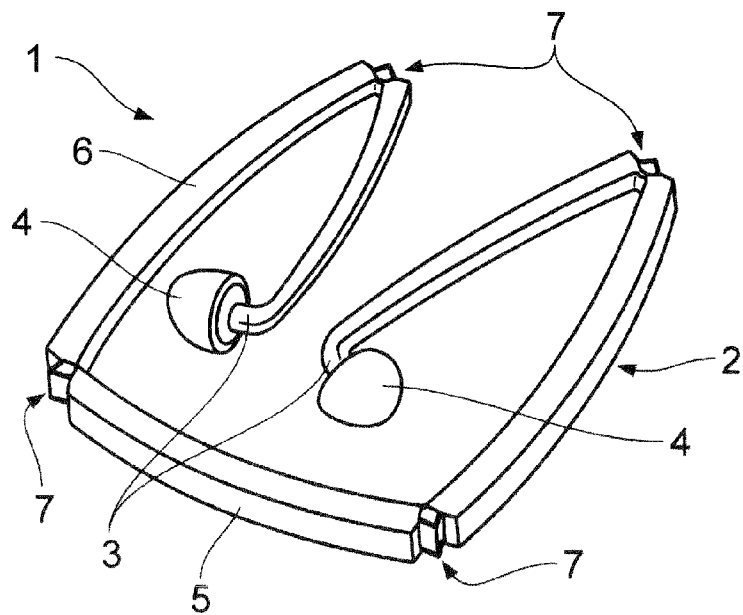
FIG. 2 shows the bow-type ear protector of FIG. 1 in the folded-up state.

Between a base 5 of the U-shaped bow 2 and each of the legs 6 of the U, a respective film hinge 7 is embodied, and each leg of the U is likewise divided by a film hinge 7, so that the ear protector 1 can be folded up, as shown in FIG. 2, for storage, for instance in a shirt or jacket pocket.

Figure 3:
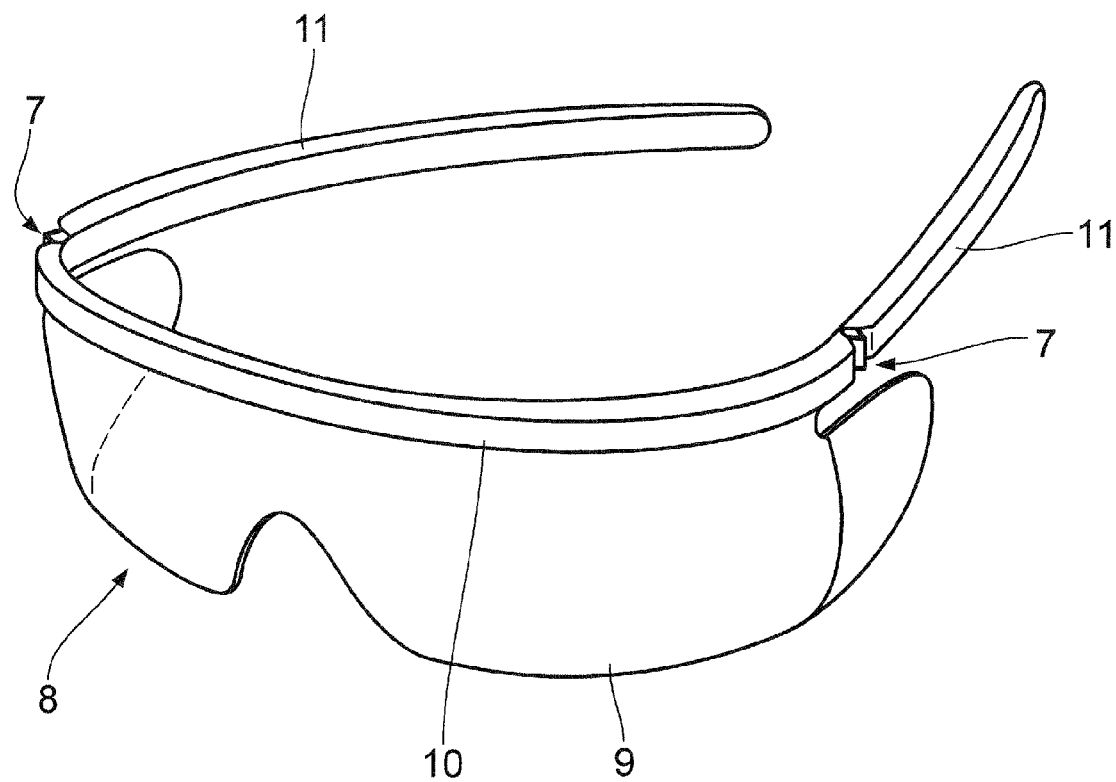
FIG. 3 shows a pair of safety work goggles, with film hinges according to the invention.

In FIG. 3, a pair of safety work goggles 8 is shown schematically, with a continuous one-piece sheet 9 and an upper frame part 10; temples 11 are pivotably connected to both ends of the upper frame part 10 via a respective strap hinge 7.

Figure 4:
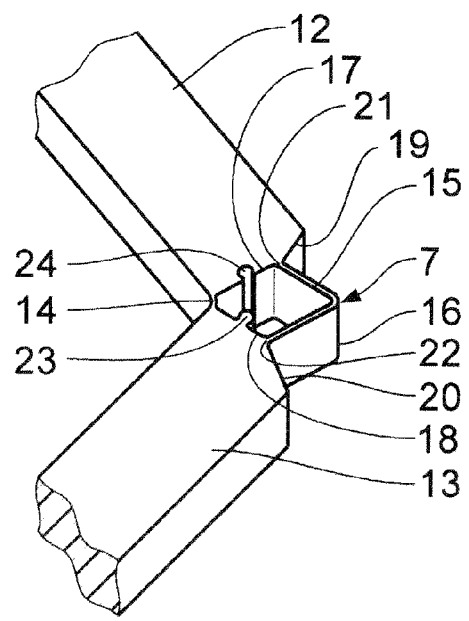
FIG. 4 is a perspective view of a film hinge according to the invention.

In FIG. 4, the film hinge 7 is shown between two parts 12, 13 that are to be joined. These parts 12, 13 to be joined may be formed by the base 5 of the U and one leg 6 of the U, in the case of the bow-type ear protector shown in FIG. 1, or by the upper frame part 10 and one temple 11, in the case of the safety work goggles 8 in FIG. 3. The hinge according to the invention, because of its low height and its resistance to torsion and the capability of being produced in one piece and economically, is also suitable for numerous other applications that involve comparable requirements.

The film hinge 7 shown in FIG. 4 includes a first strap hinge 14, injection-molded integrally with the parts 12, 13 and joining the parts 12, 13 directly to one another, and spaced apart from it a second strap hinge 15, which has a fold 16 that in the exemplary embodiment extends outward. In this way, with a fold, the second strap hinge 15 forms the joint region spanned by the first strap hinge 14.

The end faces 17, 18 of the parts 12, 13 to be joined have oblique faces 19, 20, which with the respective end faces 17, 18 form a respective edge 21, 22. The second strap hinge 15 extends from the first edge 21 to the second edge 22 and accordingly, in the extended state, comes to rest, forming a flush closure between the oblique faces 19, 20.

For stabilizing or locking the film hinge 7 in the extended state for use, a detent protrusion 23 on the first part 13 and a detent recess 24, in the form of a detent groove, on the second part 12 are provided, which mesh in locking fashion with one another in form- and force-locking fashion, when the joint is closed and when it is put in the extended state.

What is claimed is:

1. A protective device for the human body
   including a joint between two parts joined in articulated fashion, which joint has a joint opening range and is formed by a film hinge in the form of a strap hinge injection-molded integrally with the parts joined,
   wherein in addition to the first strap hinge, a second strap hinge, also injection-molded integrally with the parts joined, is provided, which can be folded up and which is disposed in the joint region at a spacing from the first strap hinge,
   wherein the second strap hinge extends across the joint opening range that is defined by the first strap hinge.

2. The protective device as defined by claim 1, wherein in a hinge region of the first strap hinge, the second strap hinge extends away from outer edges of the parts joined.

3. The protective device as defined by claim 1, wherein the parts joined each have an oblique face, opening outward and forming a chamfer, on their respective end faces in the joint region, and the second strap hinge extends inward away from the transitional edges between an end of the face and the chamfer and comes to rest, in the open state of the joint, in folded-up fashion between the chamfers.

4. The protective device as defined by claim 1, wherein the joint has no portions that protrude in the direction of the hinge axes.

5. The protective device as defined by claim 1, wherein on face ends of the parts joined in articulated fashion, at least one protrusion is provided, and on the respective other part, at least one detent recess for locking the joint in the open state is provided.

6. A protective device for the human body as defined in claim 1, wherein the protective device is a bow-type ear protector or a pair of safety work goggles.

7. A protective device for the human body
   including a joint between two parts joined in articulated fashion, which joint has a joint opening range and is formed by a film hinge in the form of a strap hinge injection-molded integrally with the parts joined,
   wherein in addition to the first strap hinge, a second strap hinge, also injection-molded integrally with the parts joined, is provided, which can be folded up and which is disposed in the joint region at a spacing from the first strap hinge,
   wherein on face ends of the parts joined in articulated fashion, at least one protrusion is provided, and on the respective other part, at least one detent recess for locking the joint in the open state is provided.

8. A protective device for the human body
   including a joint between two parts joined in articulated fashion, which joint has a joint opening range and is formed by a film hinge in the form of a strap hinge injection-molded integrally with the parts joined,
   wherein in addition to the first strap hinge, a second strap hinge, also injection-molded integrally with the parts joined, is provided, which can be folded up and which is disposed in the joint region at a spacing from the first strap hinge,
   wherein the parts joined each have an oblique face, opening outward and forming a chamfer, on their respective end faces in the joint region, and the second strap hinge extends inward away from the transitional edges between an end of the face and the chamfer and comes to rest, in the open state of the joint, in folded-up fashion between the chamfers.

* * * * *